United States Patent
Ralph et al.

(10) Patent No.: US 6,764,515 B2
(45) Date of Patent: Jul. 20, 2004

(54) INTERVERTEBRAL SPACER DEVICE UTILIZING A SPIRALLY SLOTTED BELLEVILLE WASHER AND A ROTATIONAL MOUNTING

(75) Inventors: James D. Ralph, Seaside Park, NJ (US); Thomas J. Errico, Summit, NJ (US)

(73) Assignee: SpineCore, Inc., Summit, NJ (US)

( * ) Notice: Subject to any disclaimer, the term of this patent is extended or adjusted under 35 U.S.C. 154(b) by 124 days.

(21) Appl. No.: 10/040,801

(22) Filed: Jan. 7, 2002

(65) Prior Publication Data

US 2002/0111686 A1 Aug. 15, 2002

Related U.S. Application Data

(63) Continuation-in-part of application No. 09/970,479, filed on Oct. 4, 2001.

(51) Int. Cl.$^7$ .................................................. A61F 2/44
(52) U.S. Cl. ............................... 623/17.13; 623/17.14; 623/17.15
(58) Field of Search ........................... 623/17.11, 17.13, 623/17.14, 17.15, 17.16

(56) References Cited

U.S. PATENT DOCUMENTS

| | | | |
|---|---|---|---|
| 4,917,704 A | * 4/1990 | Frey et al. | ............ 623/17.16 |
| 5,458,642 A | 10/1995 | Beer et al. | |
| 5,556,431 A | 9/1996 | Buttner-Janz | |
| 5,562,738 A | 10/1996 | Boyd et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,755,796 A | 5/1998 | Ibo et al. | |
| 5,827,328 A | 10/1998 | Butterman | |
| 5,865,846 A | 2/1999 | Bryan et al. | |
| 5,888,226 A | 3/1999 | Rogozinski | |
| 5,895,428 A | 4/1999 | Berry | |
| 5,899,941 A | 5/1999 | Nishijima et al. | |
| 5,989,291 A | 11/1999 | Ralph et al. | |
| 6,001,130 A | 12/1999 | Bryan et al. | |
| 6,019,792 A | 2/2000 | Cauthen | |
| 6,039,763 A | 3/2000 | Shelokov | |
| 6,063,121 A | 5/2000 | Xavier et al. | |
| 6,113,637 A | 9/2000 | Gill et al. | |
| 6,136,031 A | 10/2000 | Middleton | |
| 6,146,421 A | 11/2000 | Gordon et al. | |
| 6,156,067 A | 12/2000 | Bryan et al. | |
| 6,179,874 B1 | 1/2001 | Cauthen | |
| 6,228,118 B1 | 5/2001 | Gordon | |

* cited by examiner

*Primary Examiner*—Brian E Pellegrino
(74) *Attorney, Agent, or Firm*—Joseph P. Errico, Esq.; Timothy J. Bortree, Esq.

(57) ABSTRACT

An intervertebral spacer having opposing plates seatable against opposing vertebral bones, separated by at least one spring mechanism, preferably a spirally slotted belleville washer having a wide end rigidly fixed to an upper plate and a narrow end rotatably mounted to a lower plate. The lower plate includes an inwardly deflecting central post extending upwardly from the inner surface of the lower plate, the post including a head that is received through a central opening in the narrow end of the washer so that the washer is restricted from angulation with respect to the lower plate, but allowed to rotate with respect to the lower plate so that the plates can rotate relative to one another. The plates can angulate relative to one another because the washer deflects under lateral deflection forces and return to its undeflected shape when the forces are relieved.

23 Claims, 6 Drawing Sheets

INTERVERTEBRAL SPACER DEVICE UTILIZING A SPIRALLY SLOTTED BELLEVILLE WASHER AND A ROTATIONAL MOUNTING

CROSS-REFERENCE TO RELATED APPLICATION

This application is a continuation-in-part of U.S. patent application Ser. No. 09/970,479, filed Oct. 4, 2001, which is fully incorporated herein by reference.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device which utilizes a spirally slotted and rotatably mounted belleville washer as a restoring force generating element.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer that stabilizes the spine without promoting a bone fusion across the intervertebral space.

It is further an object of the present invention to provide an implant device which stabilizes the spine while still permitting normal motion.

It is further can object of the present invention to provide a device for implantation into the intervertebral space that does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. In particular, this spring mechanism provides a strong restoring force when compression and/or lateral deflection loads are applied to the plates, and also permits rotation of the two plates relative to one another. While there are a wide variety of embodiments contemplated, a preferred embodiment includes a belleville washer utilized as the restoring force providing element, the belleville washer being spirally slotted and rotatably mounted.

More particularly, as the assembly is to be positioned between the facing surfaces of adjacent vertebral bodies, the base plates should have substantially flat external surfaces that seat against the opposing bone surfaces. In as much as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to its adjacent bone, the upper and lower plates alternatively may each include outwardly directed spikes or ridges that penetrate the bone surface and mechanically hold the plates in place. However, it is more preferably anticipated that the plates should include a porous feature into which the bone of the vertebral body can grow. The most desirable upper and lower plate surface porous feature is a deflectable wire mesh into which the bone can readily grow, and which mesh will deform to seat into the concave upper and lower bone faces. (Note that this limited fusion of the bone to the base plate does not extend across the intervertebral space.) These features, while being preferred, are not required.

In some embodiments (although not in the preferred embodiment), between the base plates, on the exterior of the device, there is included a circumferential wall which is resilient and which simply prevents vessels and tissues from entering within the interior of the device This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials that could be utilized herein may be found in the orthopedic field in conjunction with ligament and tendon repair. It is anticipated that future developments in this area will produce materials that are compatible for use with this invention, the breadth of which shall not be limited by the choice of such a material.

As introduced above, the internal structure of the present invention comprises a spring member, which provides a restoring force when compressed or laterally deflected. The restoring force providing subassembly does not substantially interfere with the rotation of the opposing plates relative to one another. In the preferred embodiment, the spring subassembly is configured to allow rotation of the plates relative to one another. As further mentioned above, the force restoring member comprises at least one belleville washer that is spirally slotted.

Belleville washers are washers that are generally bowed in the radial direction. Specifically, they have a radial convexity (i.e., the height of the washer is not linearly related to the radial distance, but may, for example, be parabolic in shape). The restoring force of a belleville washer is proportional to the elastic properties of the material. In addition, the magnitude of the load support and restoring force provided by the belleville washer under compression and/or lateral deflection may be modified by providing one or more slots in the washer. In the preferred embodiment of the present invention, the belleville washer utilized as the load supporting and force restoring member is spirally slotted, with a single spiral slot initiating near the periphery of the washer and extending along an arc that is radially inwardly directed a distance toward the center of the bowed disc, and terminating near the center of the bowed disc. Preferably, the spiral slot extends around the surface of the belleville washer for more than 360 degrees and preferably 540 degrees. Additional configurations, including multiple slots, arcs of different lengths and/or arcs that extend for more or less than 360 degrees, can be used to adjust the load bearing and force restoring characteristics of the belleville washer within the scope of the present invention.

In the preferred embodiment of the present invention, a single belleville washer, which is slotted as described above, is utilized in conjunction with a rotational mounting between one end of the belleville washer and one of the opposing plates, and a rigid fixation of the other end of the belleville washer to the other of the opposing plates. The rotational mounting allows the washer to freely rotate relative to the one of the opposing plates. In as much as the washer is rigidly fixed to the other of the opposing plates, the mounting allows the opposing plates to rotate relative to one another. More particularly, this embodiment comprises a pair of spaced apart base plates, one of which is a disc shaped member (preferably shaped to match the end of an intervertebral disc) having an external face (preferably having the porous coating discussed above) and an internal face. The wide end of the belleville washer is rigidly fixed to the internal face of this base plate, preferably by laser welding. The other of the base plates is similarly shaped, having an exterior face (preferably having the porous coating discussed above), but further includes on its internal face a central post which rises out of the internal face at a nearly perpendicular angle (it should be understood that the post need not extend from the center of the plate, but rather is can be positioned according to the proper clinical placement depending on where the device is placed in the spine, In as much as a more anterior or a more posterior position may be suitable in certain parts of the spine). The central post comprises a plurality of upwardly extending members that mutually define a cylinder having a central axial bore and vertically oriented slots separating each individual member. This conformation permits the mutually defined cylindrical shape to deflect inward upon the application of a corresponding force and return to an undeflected shape once the force is relieved. Each of the upwardly extending members comprises a generally uniform radial thickness, thereby mutually defining a constant diameter for the cylinder from its union with the plate up to a circumferential position near to the uppermost extent thereof. The uppermost extent thereof, however, comprises a discontinuously widened circumference that subsequently tapers radially inwardly from that vertical position to the upper end. This discontinuously widened circumference thereby defines an annular ledge around the cylindrical top section, which ledge tapers inwardly to provide a beveled conformation. The portion of the post from the ledge to the upper end of the post is referred to herein as the head of the post. The central axial bore is threaded, and receives a small set screw. Prior to the insertion of the set screw, the post can deflect radially inward because of the axial bore and the vertically oriented slots. The insertion of the set screw eliminates the capacity for this deflection As introduced above, the spirally slotted belleville washer is mounted to this central post in such a way that it may rotate freely through a range of rotation angles equivalent to the fraction of normal human spine rotation (to mimic normal disc rotation). In this regard, the belleville washer has a flattened narrow end with a central opening. The central opening has a diameter that is greater than the diameter of the post up to the ledge, but smaller than the diameter of the head at the ledge. Therefore, the head can be passed through the central opening when the set screw is not in the axial bore, because the slots will allow the head to deflect inward when the head is forced through the central opening. Once the head has passed through the central opening, the head will return to its undeflected shape so that the narrow end is seated between the plate and the ledge. Subsequent introduction of the set screw into the axial bore eliminates the capacity for the head to deflect. Preferably, the length of the post from the plate to the ledge is slightly longer than the thickness of the washer at the narrow end, so that the washer is restricted from angulating with respect to the plate but not restricted from rotating with respect to the plate. (Angulation of the plates relative to one another will be possible because of the ability of the washer to deflect under lateral deflection forces and return to its undeflected shape.)

The assembly provides ample spring-like performance with respect to compression and lateral deflection loads, as well as long cycle life to mimic the biomechanical performance of the normal human intervertebral disc. The rigid fixation of the wide end of the belleville washer maintains the wide end against the one opposing plate. While the narrow end of the belleville washer can rotate freely relative to the other opposing plate, the narrow end is angulationally fixed relative to that plate (as described above). Therefore, not only compression, but also lateral deflection loads, are borne by the washer spring. The spiral slot of the belleville washer allows the washer to compress as the slot narrows under compression loads, only to spring back into its undeflected shape upon the unloading of the spring. Further, the spiral slot allows one side of the washer to compress and the opposite side to expand as the portion of the slot on the one side narrows and the portion of the slot on the opposite side widens under lateral deflection loads, only to spring back into its undeflected shape upon the unloading of the spring.

Finally, In as much as the human body has a tendency to produce fibrous tissues in perceived voids, such as may be found within the interior of the present invention, and such fibrous tissues may interfere with the stable and/or predicted functioning of the device, some embodiments of the present invention (although not the preferred embodiment) will be filled with a highly resilient elastomeric material. The material itself should be highly biologically inert, and should not substantially interfere with the restoring forces provided by the spring-like mechanisms therein. Suitable materials may include hydrophilic monomers such as are used in contact lenses. Alternative materials include silicone jellies and collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the present invention shall not limit the breadth thereof.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Figure 1:
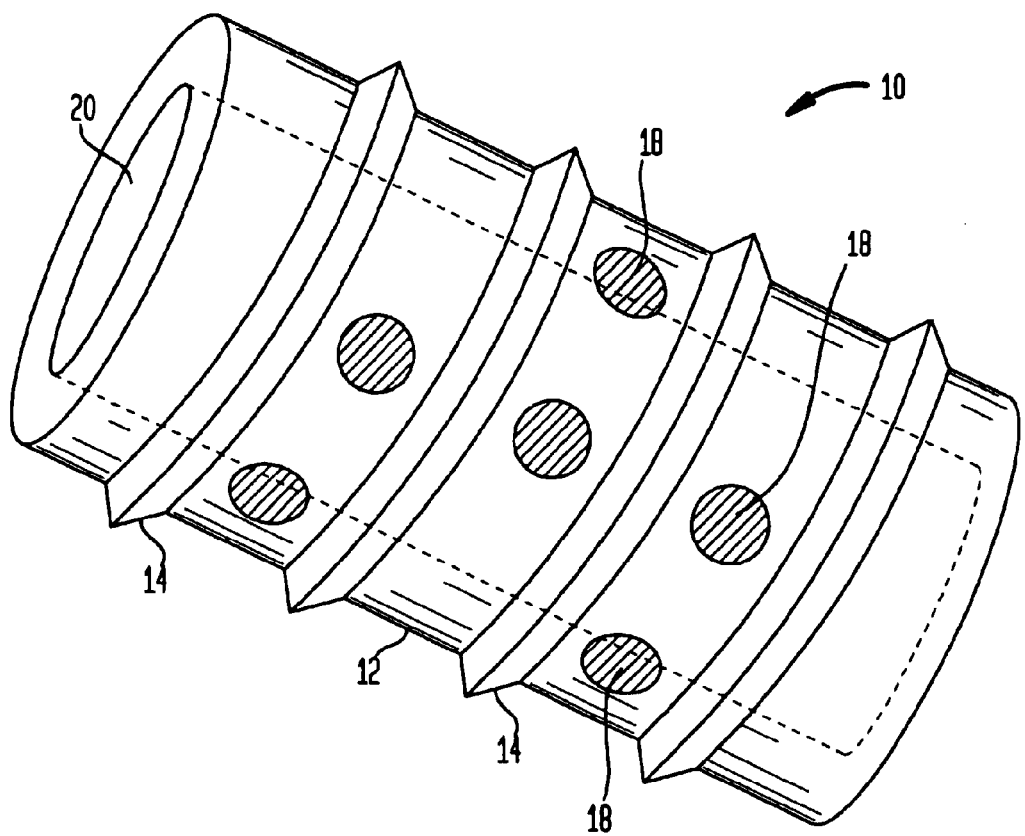
FIG. 1 is a side perspective view of an interbody fusion device of the prior art.
Figure 2:
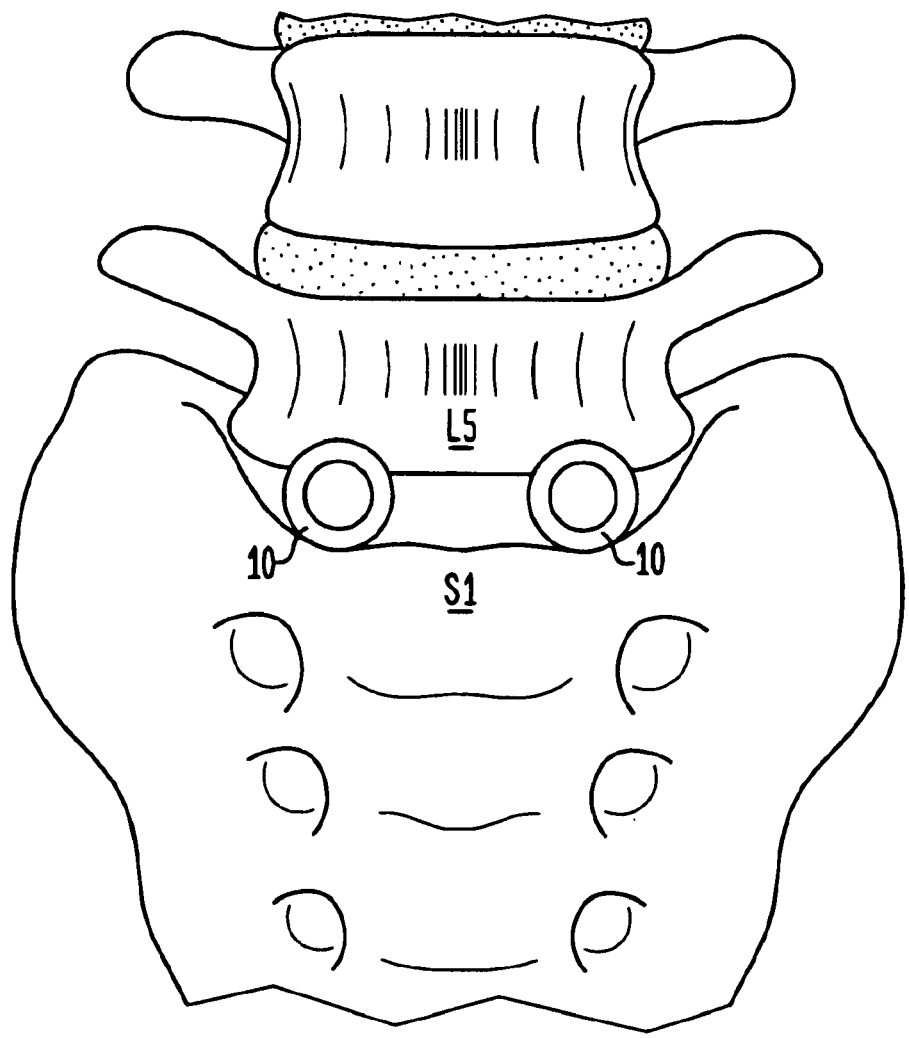
FIG. 2 is a front view of the anterior portion of the lumbo-sacral region of a human spine, into which a pair of interbody fusion devices of the type shown in FIG. 1 have been implanted.
Figure 3A:
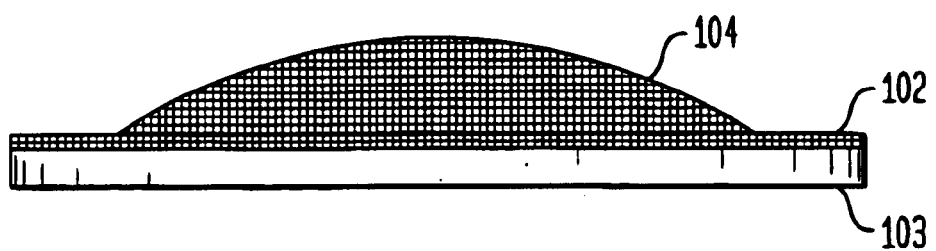
FIGS. 3a and 3b are side cross-section views of the upper and lower opposing plates of the preferred embodiment of the present invention.
Figure 3B:
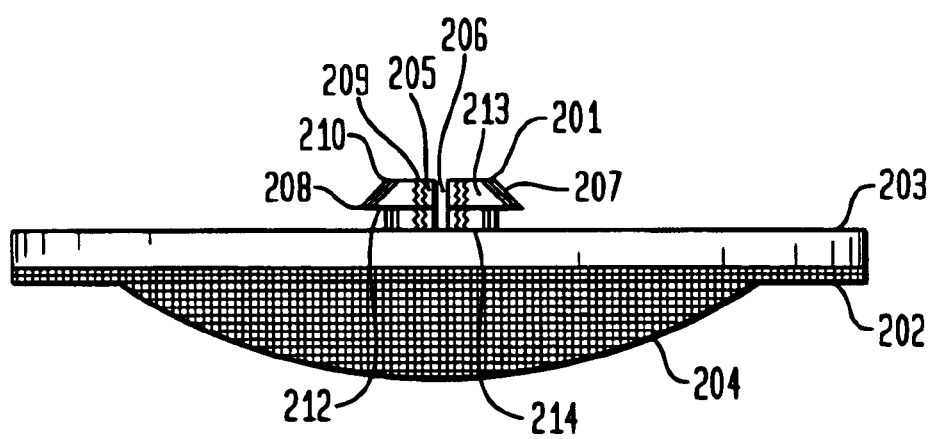

Referring now to FIGS. 3a and 3b, side cross-section views of upper and lower plate members 100, 200 of the preferred embodiment of the present invention are shown. As the device is designed to be positioned between the facing surfaces of adjacent vertebral bodies, the plates include substantially flat external face portions 102, 202 that seat against the opposing bone surfaces. In addition, the plates are to mate with the bone surfaces in such a way as to not rotate relative thereto. (The plates rotate relative to one another, but not with respect to the bone surfaces with which they are each in contact.) In order to prevent rotation of each plate relative to its adjacent bone, it is, therefore, preferred that the external faces of the plates include a porous feature 104, 204 into which the bone of the vertebral body can grow. The most desirable upper and lower plate surface porous feature is a deflectable wire mesh 104, 204 into which the bone can readily grow, and which mesh will deform to seat into the concave upper and lower bone faces. (Note that this limited fusion of the bone to the base plate does not extend across the intervertebral space.) A hole (not shown) can be provided in the upper plate such that the interior of the device may be readily accessed if a need should arise.

The upper plate 100 includes an internal face 103. The lower plate 200 includes an internal face 203 that includes a central post 201 which uses out of the internal face 203 at a nearly perpendicular angle. The central post 201 comprises a plurality of upwardly extending members 202 which mutually define a cylinder 201 having a central axial bore 209 and vertically oriented slots 206 separating each individual member 202. This conformation permits the cylinder 201 to deflect inward upon the application of a corresponding force and return to an undeflected shape once the force is relieved. Each of the upwardly extending members 202 comprises a generally uniform radial thickness, thereby mutually defining a constant diameter for the cylinder 201 from its union 204 with the internal face 203 of the lower plate 200 up to a circumferential position 208 near to the uppermost extent 210 thereof. The uppermost extent 210 thereof, however, comprises a discontinuously widened circumference which subsequently tapers radially inwardly from that vertical position to the upper end of the members 202. This discontinuously widened circumference thereby defines an annular ledge 212 around the cylindrical top section, which ledge 212 tapers inwardly to provide a beveled conformation. The portion of the post 201 from the ledge 212 to the upper end of the post 201 is referred to herein as the head 207 of the post 201. The central axial bore 209 is threaded and is designed to receive a set screw 205. Prior to the insertion of the set screw 205, the post 201 can deflect radially inward because of the axial bore 209 and the vertically oriented slots 206. The insertion of the set screw 205 eliminates the capacity for this deflection.

Figure 4A:
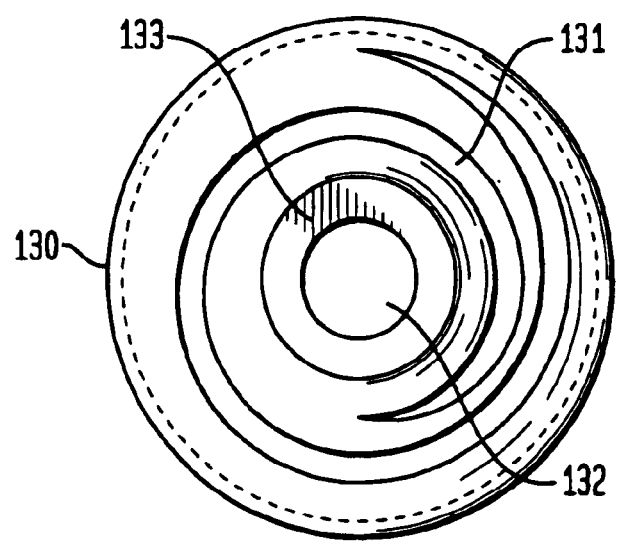
FIGS. 4a and 4b are top and side cross-section view of a belleville washer having a spiral slot, for use in a preferred embodiment of the present invention.
Figure 4B:
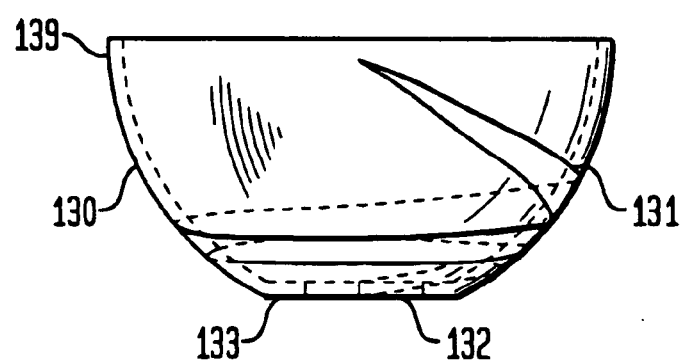

Referring now to FIGS. 4a and 4b, a spirally slotted belleville washer 130 is provided in top and side cross-section views, respectively. The belleville washer 130 is a restoring force providing device which comprises a circular shape, having a wide end 139 and a flattened narrow end 133 with a central opening 132, and which is radially arched in shape. The belleville washer 130 has a radial convexity (i.e., the height of the washer 130 is not linearly related to the radial distance, but may, for example, be parabolic in shape). The restoring force of the belleville washer 130 is proportional to the elastic properties of the material.

The belleville washer 130 has a spiral slot 131 formed therein. The slot 131 extends from a point near the periphery of the wide end 139 of the washer 130, along an arc that is radially inwardly directed a distance toward a the center of the washer 130, and terminates at a point near the central opening 132, preferably where the flatness of the flattened narrow end 133 begins. In preferred embodiments, the slot 131 extends around the surface of the belleville washer 130 for more than 360 degrees, and most preferably, for 540 degrees as shown. Additional configurations, including multiple slots, arcs of different lengths and/or arcs that extend for more or less than 360 degrees, can be used to adjust the load bearing and force restoring characteristics of the belleville washer 130 within the scope of the present invention, depending upon the requirements of the patient, and the anatomical requirements of the device.

The central opening 132 of the belleville washer 130 is dimensioned to receive the head 207 of the post 201 of the lower plate 200 described above. More particularly, the diameter of the central opening 132 is greater than the diameter of the cylinder 201 from the union 204 with the internal face 203 of the lower plate 200 up to the ledge 212, but smaller than the diameter of the head 207 at the ledge 212. Therefore, the head 207 can be passed through the central opening 132 when the set screw 205 is not in the axial bore 209, because the slots 206 will allow the head 207 to deflect inward when the head 207 is forced through the central opening 132. Once the head 207 has passed through the central opening 132, and consequently the force causing the deflection of the head 207 is relieved, the head 207 will return to its undeflected shape so that the narrow end 133 is seated between the internal face 203 of the lower plate 200 and the ledge 212 of the post 201. Subsequent introduction of the set screw 205 into the axial bore 209 eliminates the capacity for the head 207 to deflect, ensuring that the head 207 cannot back through the opening 132 without removal of the set screw 205. Preferably, as shown, the length of the post 201 from the internal face 203 of the lower plate 200 to the ledge 212 is slightly larger than the thickness of the washer 130 at the narrow end 133, so that the washer 130 is restricted from angulating with respect to the lower plate 200 but not restricted from rotating with respect to the lower plate 200. (Angulation of the plates relative to one another will be possible because of the ability of the washer 130 to deflect under lateral deflection forces and return to its undeflected shape.) It should be noted that the flat configuration of the narrow end 133 of the washer 130 facilitates this preferable fitting of the narrow end 133 between the ledge 212 and the plate 200.

Figure 5A:
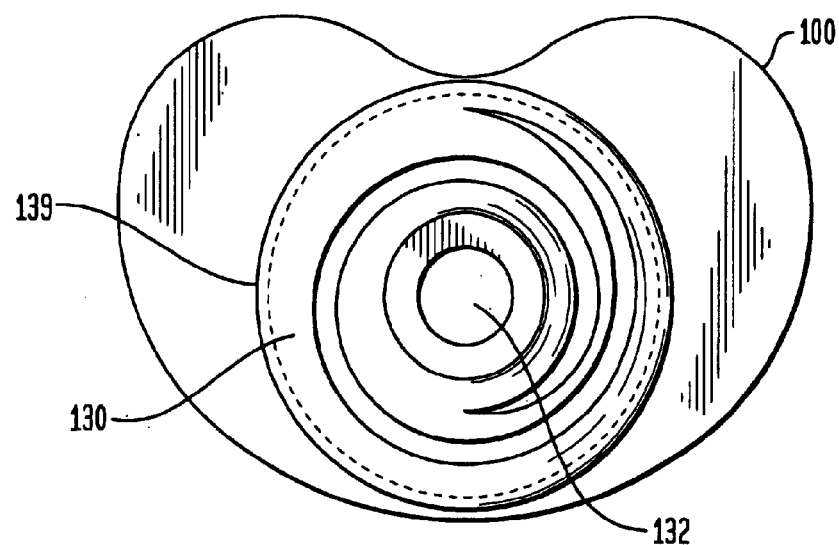
FIG. 5a is a top view of the upper plate of FIG. 3a, with the wide end of the belleville washer of FIGS. 4a and 4b rigidly fixed to the upper plate.
Figure 5B:
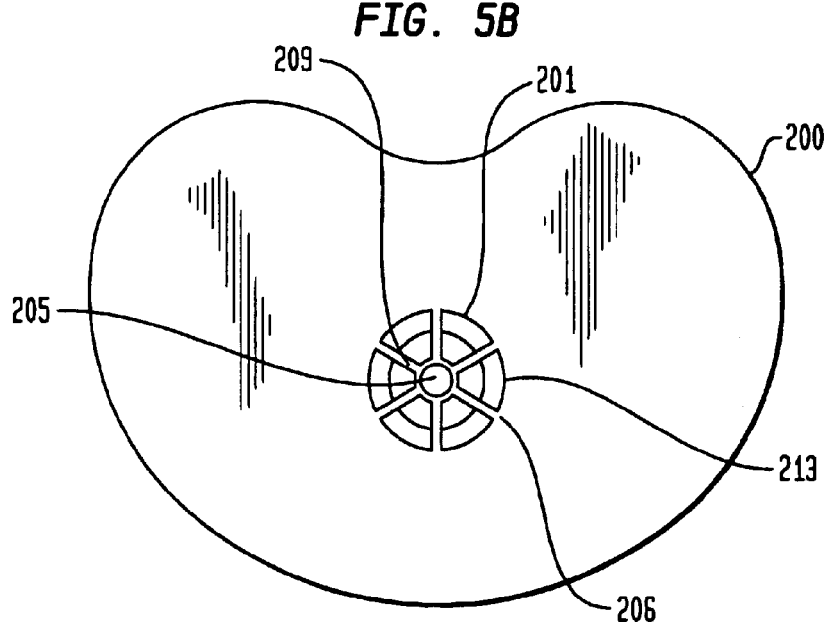
FIG. 5b is a top view of the lower plate of FIG. 3b.

Referring now to FIG. 5a, a top view of the upper plate 100 of FIG. 3a, with the wide end 139 of the spirally slotted belleville washer 130 of FIGS. 4a and 4b rigidly secured thereto, preferably by laser welding the wide end 139 to the upper plate 100, is shown. FIG. 5b shows a top view of the lower plate 200 of FIG. 3b, showing the set screw 205 in the axial bore 209 of the post 201.

Figure 6:
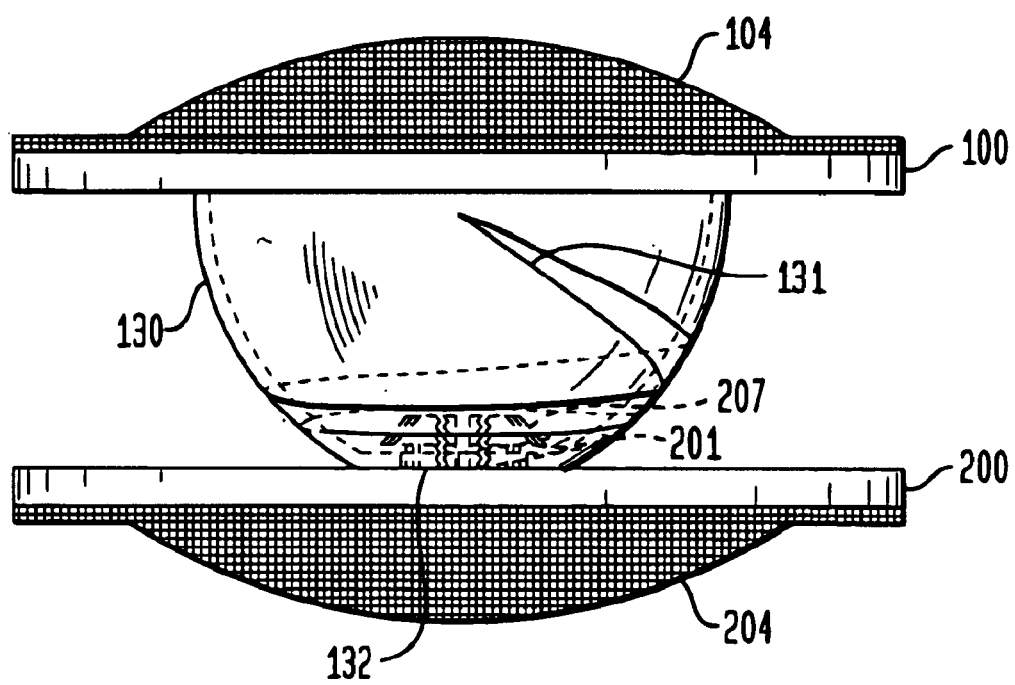
FIG. 6 is a side cross-section view of the preferred embodiment of the present invention, which utilizes a belleville washer of the type shown in FIGS. 4a and 4b, showing the plates of FIGS. 6a and 6b assembled together.

FIG. 6 shows the fully assembled preferred embodiment of the present invention. The spirally slotted belleville washer 130 of FIGS. 4a and 4b is placed with its wide end rigidly fixed against the top plate 100 as shown in FIG. 5a. The head 207 of the post 201 of the lower plate 200 is fitted into the central opening 132 of the belleville washer 130 as described above, so that the washer 130 cannot be readily removed therefrom, but can still rotate thereon. Thereafter, the device can be placed between two vertebral bodies, with the porous features 104, 204 facilitating bore growth thereinto and securing the plates 100, 200 to the adjacent bones. Loading of the assembly under normal motion causes the washer 130 to deflect (with the spiral slot 131 enhancing the deflection). More particularly, the spiral slot of the belleville washer allows the washer to compress as the slot narrows under compression loads, only to spring back into its undeflected shape upon the unloading of the spring. Further, the spiral slot allows one side of the washer to compress and the opposite side to expand as the portion of the slot on the one side narrows and the portion of the slot on the opposite side widens under lateral deflection loads, only to spring back into its undeflected shape upon the unloading of the spring.

In as much as the human body has a tendency to produce fibrous tissues in perceived voids, such as may be found within the interior of the present invention, and such fibrous tissues may interfere with the stable and/or predicted functioning of the device, some embodiments of the present invention (although not the preferred embodiment) will be filled with a highly resilient and biologically inert elastomeric material. Suitable materials may include hydrophilic monomers such as are used in contact lenses. Alternative materials include silicone jellies and collagens such as have been used in cosmetic applications.

While there has been described and illustrated specific embodiments of an intervertebral spacer device, it will be apparent to those skilled in the art that variations and modifications are possible without deviating from the broad spirit and principle of the present invention. The invention, therefore, shall not be limited to the specific embodiments discussed herein.

We claim:

1. An intervertebral spacer device, comprising:
    first and second plates, each having an outwardly facing plate surface and an inwardly facing plate surface, the plates being disposed such that the inwardly facing plate surfaces are directed toward one another and the outwardly facing plate surfaces are directed away from one another; and
    at least one restoring force providing element disposed between said inwardly facing surfaces, and disposed such that a load applied to the outwardly facing surfaces is counteracted by the at least one restoring force providing element;

the at least one restoring force providing element including a belleville washer having a first end and a second end, the belleville washer being rigidly fixed at the first end to the inwardly facing surface of the first plate and rotationally mounted at the second end to the inwardly facing surface of the second plate; and wherein the belleville washer has a spiral slot.

2. The intervertebral spacer device of claim 1, further comprising a post structure extending from the inwardly facing surface of the second plate, the post structure having a central longitudinal axis and ahead, and wherein the belleville washer has a central opening at the second end of the belleville washer, trough which the head is mountable to allow the second end of the belleville washer to rotate about the central longitudinal axis and to limit other movement of the second end of the belleville washer relative to the central longitudinal axis.

3. The intervertebral spacer device of claim 2, wherein the post structure is deflectable toward die central longitudinal axis into a deflected state upon the application of a corresponding force, and returnable to an undeflected state upon relief from the force, and wherein the central opening of the belleville washer has a diameter, the post structure has a diameter smaller than the diameter of the central opening, the head of the post structure has a diameter greater than the diameter of the central opening in the undeflected state of the post structure and a diameter smaller than the diameter of the central opening in the deflected state of the post structure, the belleville washer has a thickness adjacent the central opening, and the post structure has a length greater than the thickness of the belleville washer adjacent the central opening.

4. The intervertebral spacer device of claim 3, wherein the post structure comprises a plurality of post members separated from one another by a plurality of slots, each of the post members being deflectable toward one another, each of the post members having a member head, the members collectively forming the post structure, the member heads collectively forming the head of the post structure.

5. The intervertebral spacer device of claim 3, wherein deflection of the post structure under the force is preventable.

6. The material spacer device of claim 5, wherein the post structure comprises a central threaded bore adapted to receive a screw, and disposition of the screw within the central threaded bore prevents the post from deflecting toward the central longitudinal axis of the poet structure, and withdrawal of the screw from the central threaded bore allows the post structure to deflect toward the central longitudinal axis of the post structure.

7. The intervertebral spacer device of claim 3, wherein the second end has a flat portion which the central opening is formed, the flat portion having a diameter greater than the diameter of the head that is greater than the diameter of the central opening in the undeflected state of the poet structure.

8. The intervertebral spacer device of claim 7, wherein the spiral slot extends from of the belleville washer along an arc that is radially inwardly directed toward a center of the belleville washer.

9. The intervertebral spacer device of claim 8, wherein the spiral slot extends for at least a 360 degree turn.

10. The intervertebral spacer device of claim 9, wherein the spiral slot extends for a more than 360 degree turn.

11. The intervertebral spacer device of claim 1, wherein each of the outwardly facing surfaces has a porous feature suitable for bone ingrowth.

12. The intervertebral spacer device of claim 11, wherein the porous feature comprises a wire mesh.

13. It An intervertebral spacer device, comprising:
first and second plates, each having an outwardly facing surface and a inwardly facing surface, the plates being disposed such that the inwardly facing surfaces face one another;
a spring having a first end and a second end and a longitudinal axis, the find end being rigidly mounted to the first plate, the second end being mounted to the second plate for rotational movement of the second end of the spring about the longitudinal axis relative to the second plate and for limited other movement of the second end of the spring relative to the second plate;
wherein the spring comprises a belleville washer;
wherein the first end of the spring is a wide end of the belleville washer and the second end of the spring is a narrow end of the belleville washer;
wherein the belleville washer has at least one spiral slot.

14. The intervertebral spacer device of claim 13, wherein the spiral slot extends from near a periphery of the belleville washer along an arc that is radially inwardly directed toward a center of the belleville washer.

15. An intervertebral spacer device, comprising:
first and second plates, each having an outwardly facing surface and a inwardly facing surface, the plates being disposed such that the inwardly facing surfaces face one another;
a spring having a first end and a second end and a longitudinal axis, the first end being rigidly mounted to the first plate, the second end being mounted to the second plate for rotational movement of the second end of the wring about the longitudinal axis relative to the second plate and for limited other movement of the second end of the spring relative to the second plate;
wherein the second plate comprises a central structure extending from the inwardly facing surface of the second plate, the central structure having a radially outwardly extending ledge parallel to the inwardly facing surface of the second plate, and wherein the second end of the spring has a central opening through which the central structure is disposable to seat the second end of the spring between the ledge and the inwardly facing surface of the second plate, such that interference of the second end of the spring with the ledge and the inwardly facing surface of the second plate limits movement of the second end of the spring along the longitudinal axis relative to the second plate.

16. The intervertebral spacer device of claim 15, wherein a minimum distance between the ledge and the inwardly facing surface of the second plate accommodates a maximum thickness of the second end of the spring such that the spring is free to rotate about the longitudinal axis relative to the second plate.

17. The intervertebral spacer device of claim 15, wherein the spring comprises a belleville washer.

18. The intervertebral spacer device of claim 17, wherein the first end of the spring is a wide end of the belleville washer and the second end of the spring is a narrow end of the belleville washer.

19. The intervertebral spacer device of claim 18, wherein the belleville washer has at least one spiral slot.

20. An intervertebral spacer device, comprising:
first and second plates, each having an outwardly facing plate surface and an inwardly facing plate surface, the plates being disposed such that the inwardly facing plate surfaces are directed toward one another and the outwardly facing plate surfaces are directed away from one another; and at least one restoring force providing element disposed between said inwardly facing surfaces, and disposed such that a load applied to the outwardly facing surfaces is counteracted by the at least one restoring force providing element;

the at least one restoring force providing element including a belleville washer having a first end and a second end, the belleville washer being rigidly fixed at the first end to the inwardly facing surface of the first plate and rotationally mounted at the second end to the inwardly facing surface of the second plate;

further comprising a post structure extending from the inwardly facing surface of the second plate, the post structure having a central longitudinal axis and a bead, and wherein the belleville washer has a central opening at the second end of the belleville washer, through which the head is mountable to allow the second end of the belleville washer to rotate about the central longitudinal axis and to limit other movement of the second end of the belleville washer relative to the central longitudinal axis;

wherein the post structure is deflectable toward the central longitudinal axis into a deflected state upon the application of a corresponding force, and returnable to an undeflected state upon relief from the force, and wherein the central opening of the Belleville washer has a diameter, the post structure has a diameter smaller than the diameter of the central opening, the head of the post structure has a diameter greater than the diameter of the central opening in the undeflected state of the post structure and a diameter smaller than the diameter of the central opening in the deflected state of the post structure, the Belleville washer has a thickness adjacent the central opening, and the post structure has a length greater than the thickness of the Belleville washer adjacent the central opening, wherein the post structure comprises a plurality of post members separated from one another by a plurality of slots, each of the post members being deflectable toward one another, each of the post members having a member head, the members collectively forming the post structure, the member heads collectively forming the head of the post structure.

21. The intervertebral spacer device of claim 20, wherein the post structure comprises a central threaded bore adapted to receive a screw, and disposition of the screw within the central threaded bore prevents the post from deflecting toward the central longitudinal axis of the post structure, and withdrawal of the screw from the central threaded bore allows the post structure to deflect toward the central longitudinal axis of the post structure.

22. The intervertebral spacer device of claim 20, wherein each of the outwardly facing surfaces has a porous feature suitable for bone ingrowth.

23. The intervertebral spacer device of claim 22, wherein the porous feature comprises a wire mesh.

* * * * *

UNITED STATES PATENT AND TRADEMARK OFFICE
CERTIFICATE OF CORRECTION

PATENT NO. : 6,764,515 B2
DATED : July 20, 2004
INVENTOR(S) : James D. Ralph and Thomas J. Errico It is certified that error appears in the above-identified patent and that said Letters Patent is hereby corrected as shown below:

Column 9,
Line 15, "trough" should read -- through --.
Line 21, "die" should read -- the --.
Line 44, "material" should read -- intervertebral --.
Lines 48 and 56, "poet" should read -- post --.
Line 53, after "portion" insert -- is --.
Line 57, "7" should read -- 1 --.
Line 58, after "from" insert -- near a periphery --.
Line 61, "8" should read -- 7 --.

Column 10,
Line 3, cancel "It".
Lines 5 and 27, "a" should read -- an --.
Line 34, "wring" should read -- spring --.

Column 11,
Line 18, "bead" should read -- head --.

Signed and Sealed this

Eighteenth Day of January, 2005

JON W. DUDAS
*Director of the United States Patent and Trademark Office*